United States Patent [19]

Ritter

[11] 4,385,153
[45] May 24, 1983

[54] STABLE, AEROBICALLY-HARDENING ADHESIVES CONTAINING BORON COMPOUND INITIATORS

[75] Inventor: Wolfgang Ritter, Dusseldorf, Fed. Rep. of Germany

[73] Assignee: Henkel Kommanditgesellschaft auf Aktien, Dusseldorf-Holthausen, Fed. Rep. of Germany

[21] Appl. No.: 318,443

[22] Filed: Nov. 5, 1981

[30] Foreign Application Priority Data

Nov. 6, 1980 [DE] Fed. Rep. of Germany ....... 3041904

[51] Int. Cl.$^3$ ............................................ C08C 33/00
[52] U.S. Cl. .................................. 524/522; 523/120;
524/523; 524/556; 524/560; 526/134; 526/196;
526/317; 526/328; 526/328.5
[58] Field of Search ................ 526/134, 196; 523/120;
524/522, 523, 560, 556

[56] References Cited

U.S. PATENT DOCUMENTS 4,167,616  9/1979  Bollinger ............................. 526/197

Primary Examiner—Joseph L. Schofer
Assistant Examiner—Bernard Lipman
Attorney, Agent, or Firm—Hammond & Littell, Weissenberger and Muserlian

[57] ABSTRACT

A stable, fluid or spreadable, aerobically-hardening adhesive, storable without hardening under exclusion of oxygen, containing polymerizable olefinically-unsaturated compounds and an amount sufficient to initiate polymerization of an organoboron compound initiator, in the form of an aerobically-hardening single-component mixture, consisting essentially of:

(a) at least one organoboron compound capable of initiating the polymerization of ethylenically-unsaturated compounds in the presence of oxygen, in an amount sufficient to initiate the polymerization, (b) at least one polymerizable compound containing at least one ethylenic double bond with a molecular weight of between 63 and 10,000

(c) at least one compound capable of inhibiting and/or stabilizing anionic polymerization, in an amount sufficient to inhibit and/or stabilize anionic polymerization, and (d) optionally, other conventional auxiliary substances for aerobically-hardening adhesives.

The adhesives harden spontaneously in the presence of oxygen in a short time to give stable adhesive bonds, even in the presence of moisture.

23 Claims, No Drawings

STABLE, AEROBICALLY-HARDENING ADHESIVES CONTAINING BORON COMPOUND INITIATORS

BACKGROUND OF THE INVENTION

The invention relates to stable adhesive compositions based on compounds containing ethylenic double bonds, which also contain organoboron compounds as initiators and which harden under the action of oxygen. Described here are particularly single-component cold-hardening reaction adhesives which are preferably based on methacrylic acid derivatives.

Adhesives which harden by polymerization of compounds containing ethylenic double bonds have been known for a long time. They can be prepared from methacrylic acid esters or acrylic acid esters of various alcohols by the addition of peroxides or hydroperoxides, as initiators, and other auxiliary adjuvants. Besides these, adhesive agents and filling agents are known for use in dentistry and surgery which contain, in addition to acrylic acid esters or methacrylic acid esters and other reaction partners containing ethylenic double bonds, trialkylboron compounds, such as triethylboron, tri-n-butylboron, etc., as an essential component. Such trialkylboron compounds have the disadvantage, however, that they are readily flammable, so that the handling of these adhesives presents considerable difficulties. It has tried to eliminate this inconvenience by reacting the trialkylboron compounds with 0.3 to 0.9 mol of oxygen.

It has also been tried to react the trialkylboron compounds with amines to reduce the spontaneous ignition. Due to these measures, the ignition temperature is displaced into a range of 0° to 70° C., but there is still considerable uncertainty in the handling of these mixtures. In particular, they are not suitable for structural bonding.

The polymerization systems described so far which use organoboron compounds as reaction initiator, are so-called binary systems, that is, the olefin containing portion to be polymerized are mixed with the separately stored organoboron compound only when their polymerization immediately following is intended. This applies particularly to cold-hardening systems, that is, for reaction mixtures which are to be subjected to polymerization at room temperature or at best at moderately elevated temperatures. Examples of such reaction systems using organoboron compounds as starters or initiators are described in DOS No. 23 21 215, U.S. Pat. No. 4,167,616 and British Pat. No. 1,113,722.

OBJECTS OF THE INVENTION

An object of the present invention is to provide aerobically-hardening adhesive compositions based on ethylenically-unsaturated polymerizable compounds using organoboron compounds as reaction initiators which are sufficiently stable against polymerization under the exclusion of oxygen, but still contain the polymerizable olefinically-unsaturated components in admixture with the organoboron compounds and are cold-hardening with access of oxygen.

Another object of the present invention is the development of a stable, fluid or spreadable, aerobically-hardening adhesive, storable without hardening under exclusion of oxygen, containing polymerizable olefinically-unsaturated compounds and an amount sufficient to initiate polymerization of an organoboron compound initiator, in the form of an aerobically-hardening single-component mixture, consisting essentially of:

(a) at least one organoboron compound capable of initiating the polymerization of ethylenically-unsaturated compounds in the presence of oxygen, in an amount sufficient to initiate the polymerization, (b) at least one polymerizable compound containing at least one ethylenic double bond with a molecular weight of between 63 and 10,000, (c) at least one compound capable of inhibiting and/or stabilizing anionic polymerization, in an amount sufficient to inhibit and/or stabilize anionic polymerization, and (d) optionally, other conventional auxiliary substances for aerobically-hardening adhesives.

A further object of the present invention is the development of a reaction adhesive hardenable spontaneously by chemical reaction, which is safe to handle and leads to firm bonds with feasible service lives, even on those materials which dry very poorly. Such single-component reaction mixtures can be used in many ways, e.g., as casting resins and fillers, but particularly as adhesives.

These and other objects of the invention will become more apparent as the description thereof proceeds.

DESCRIPTION OF THE INVENTION

The invention, therefore, concerns in a first embodiment fluid or spreadable aerobically-hardenable adhesives based on polymerizable, ethylenically-unsaturated compounds which are stable under exclusion of oxygen, and contain organoboron compounds as initiators, which are characterized in that they are present as aerobically-hardening single-component mixtures, and consist substantially of:

(a) organoboron compounds capable of initiating the polymerization of ethylenically-unsaturated compounds, (b) at least one compound containing an ethylenic double bond with a molecular weight of between about 63 and 10,000, (c) inhibitors or stabilizers against anionic polymerization, as well as, (d) optionally, additional auxiliary substances, like stabilizers against free-radical polymerization, thickeners, auxiliary monomers, dyes and pigments.

More particularly, the present invention relates to a stable, fluid or spreadable, aerobically-hardening adhesive, storable without hardening under exclusion of oxygen, containing polymerizable olefinically-unsaturated compounds and an amount sufficient to initiate polymerization of an organoboron compound initiator, in the form of an aerobically-hardening single-component mixture, consisting essentially of:

(a) at least one organoboron compound capable of initiating the polymerization of ethylenically-unsaturated compounds in the presence of oxygen, in an amount sufficient to initiate the polymerization, (b) at least one polymerizable compound containing at least one ethylenic double bond with a molecular weight of between 63 and 10,000, (c) at least one compound capable of inhibiting and/or stabilizing anionic polymerization, in an amount sufficient to inhibit and/or stabilizer anionic polymerization, and (d) optionally, other conventional auxiliary substances for aerobically-hardening adhesives.

In other embodiments, the invention concerns a method for the production of these stable, fluid or spreadable aerobically-hardenable adhesives, as well as their use particularly as single component or reaction adhesives for bonding metal, wood, glass, ceramic material, and plastics, as well as in dentistry and surgery.

In a particularly important embodiment, the invention concerns single component, aerobically-hardening high-strength structural adhesives which are characterized substantially by a content of at least one polymerizable monomer, one or more boron alkyls, suitable stabilizers against premature polymerization, one or more polymers to increase the cohesion and to adjust to the desired viscosity.

The adhesive mixture is produced under complete exclusion of oxygen, working preferably under a protective gas atmosphere of pure nitrogen or noble gases, like argon, etc. The adhesive hardens as soon as the mixture comes in contact with air. The time of exposure to air to hardening (or open time) can be varied within wide limits.

The organoboron compounds serving as initiators can be added as such to the reactive masses, but they can also be formed, in a preferred embodiment of the invention, at least partly in situ by reaction of boron hydride compounds and olefinically-unsaturated components of the reactive masses. The organoboron compounds suitable as initiators or starters contain at least one boron-carbon bond, preferably at least two such boron-carbon bonds. In general, all three valences of boron used in the reactive masses are linked to carbon or hydrocarbon moieties. Suitable are both boroalkyl compounds and boroaryl compounds. Preferably at least one valence of the boron is linked to an aliphatic carbon atom. A particularly preferred class of organoboron compounds are accordingly boron alkyls with the same or different alkyl radicals. The alkyl can be linear or branched, or can even be a cycloalkyl, and these alkyls or cycloalkyls in turn can be closed to form one or several ring systems. Each alkyl can have, for example, up to 24 carbon atoms. The alkyls are preferably saturated. In addition to, or instead of, the alkyls, hydrocarbon aryls can be linked to boron. Preferably, these are mononuclear aryl, but higher molecular weight substituents, particularly binuclear aryls, are not excluded.

If the organoboron compounds used as starters are not inserted as such into the adhesive compositions, but formed in situ in the mass or in a part of the reaction mass, it is necessary to distinguish between the boron compounds to be used in the production method and the organoboron compounds found in the reactive single-component mass. In this embodiment, the invention utilizes the fact that boron hydride compounds react generally and without any difficulty, with olefin double bonds by adding boron hydride valence across the carbon double bond. It is thus possible to use, in the production of the reactive single-component mixtures, boron hydride compounds for the in situ formation of the initiator or starter. Suitable are both diborane and organoboron hydrides with one or two hydrocarbon radicals attached onto the boron.

The boron-hydrogen bonds present react normally at room temperature with sterically unhindered olefin double bonds, forming additional boron-carbon bonds.

Because of the easy flammability of the low molecular weight boron alkyls, it may be advisable for practical reasons to select from the large class of known organoboron compounds those components which are less flammable. This facilitates the production of the reaction masses. But it was found that in the finished reaction masses of the invention, the organoboron compounds which are homogeneously distributed in only limited amounts are harmless, even if these starter compounds as such are readily flammable.

Boron compounds acting as initiators include numerous boron alkyls, which are known or can be produced in known manner. Typical representatives of these boron compounds are, for example:
9-borabicyclo[3,3,1]-nonane
diisopinocampheylborane
dicyclohexylborane
thexylborane(2,3-dimethyl-2-butyl-borane)
3,5-dimethyl borinane
diisoamylborane.

Among these compounds, the first-mentioned 9-borabicyclo[3,3,1]-nonane is preferred for practical reasons. The above-mentioned compounds can be produced, for example, from the reaction of sodium borohydride or boron trifluoride with suitable olefins or diolefins. In the preparation of diborane, its ether, amine or sulfide complexes can also be used.

A list of production possibilities of suitable boron compounds can be found in the monography of Herbert C. Brown, 1975 "Organic Synthesis via Boranes," published by John Wiley & Sons. The initiators also include trialkyl boranes, as well as boron hydride reaction products from boron-hydrogen and olefins, like monoalkyl boranes and dialkyl boranes.

Suitable as olefins in the above reaction are lower alkenes, such as ethene, propene, butene, isobutene, hexene; cyclohexene; lower alkenyl halides and amines, such as vinyl chloride, allyl chloride, allyl amine; or unsaturated esters, such as methyl methacrylate, vinyl acetate or methyl crotonate. Worth mentioning among the suitable compounds are, for example:
trimethyl boron
triethyl boron
tripropyl boron
isomeric tributylborons
isomeric trihexyl borons
diisopinocampheyl-butyl boron
thexyl-cyclohexyl-cyclopentyl boron
thexyl-limonyl boron
trinorbornyl boron
B-butyl-9-borabicyclo[3,3,1]nonane
B-isobutyl-9-borabicyclo[3,3,1]nonane
B-[2-(4-cyclohexenyl)-ethyl]-9-borabicyclo[3,3,1]nonane
B-cyclopropyl-9-borabicyclo[3,3,1]nonane
B-p-tolyl-9-borabicyclo[3,3,1]nonane
B-tert.-butyl-3,5-dimethylborinane.

Other typical representatives of suitable boron compounds are the reaction product of 1,2-dihydroxybenzene with boron hydride (catechol borane) and tri-n-butylboroxine. Alkylated ($C_{1-9}$)-dihydroxybenzene can also be used as one of the starting materials.

The initiators are employed in amounts of up to 15% by weight, particularly 0.01% to 15% by weight, based on the polymerizable portion of the reaction mass. Amounts of at least about 0.1% by weight of the organoboron compounds are particularly preferred, and here again the range of about 0.1% to 10% by weight, based on the polymerizable portion of the reaction mass, are particularly important ranges in the selection of suitable reactive boron compounds.

The total amount of the initiator or starter can be added to the reaction mass from the beginning or be formed there in situ, but in a preferred embodiment to be described below, only a portion of the starter compound is charged in the production of the reactive masses, while the second portion still is added in a final stage to the reaction mass or formed there in situ.

Numerous compounds containing ethylenic double bonds can be used as the polymerizable component of the reactive adhesive compositions according to the invention. For the most important sector of the single-component reaction adhesives, are particularly important derivatives of methacrylic acid and/or acrylic acid, hereafter called (meth)acrylic acid derivatives.

Particularly important here are the esters and/or acid amides of these components, where the acid amides can be substituted in turn in the amide nitrogen. Suitable are, for example, the (meth)acrylic esters of monohydric alcohols, particularly alkanols having from 1 to 12 carbon atoms, such as methyl (meth)acrylate, ethyl (meth)acrylate, butyl (meth)acrylate, and ethylhexyl (meth)acrylate, the (meth)acrylic acid esters of polyhydric alcohols, such as ethylene glycol, diethylene glycol, polyethylene glycol, and trimethylol propane, the di- and mono(meth)acrylic acid esters of glycerin, the di(meth)acrylic acid esters of triethylene glycol and tetraethylene glycol, the di(meth)acrylic acid esters of dipropylene glycol, tripropylene glycol, tetrapropylene glycol and pentapropylene glycol, the di(meth)acrylic esters of ethoxylated or propoxylated diphenylolpropane. (Meth)acrylic acid esters of alcohols are also suitable that are derived from dihydroxymethyl tricyclodecane or also those that were prepared on a basis of tricyclodecane having two alcoholic functions in the ring system, which has been extended by reaction with dicarboxylic acids, such as maleic acid or also cyclohexanedicarboxylic acid or terephthalic acid.

Further suitable are reaction products of the diglycidyl ether of diphenylpropane with methacrylic acid and/or acrylic acid. Also useful are reaction products of diisocyanates or triisocyanates, for example, toluylene diisocyanate, diphenylmethane diisocyanate, isophorone diisocyanate, trimerized toluylene diisocyanate and similar substances with hydroxyalkyl (meth)acrylates, as polymerizable components.

Basically suitable are also polymerizable monomers, such as vinyl acetate; vinyl halides, such as vinyl chloride, vinyl fluoride, vinyl bromide; styrene; divinyl-benzene; crotonic acid esters and maleic acid esters or the so-called, if desired, styrenized, unsaturated polyester resins. These compounds generally are used only in subordinate amounts in the reaction adhesives.

Further suitable are:
2-acryloyloxyethyl phosphate
2-methacryloyloxyethyl phosphate
bis-2-acryloyloxyethyl phosphate
bis-2-methacryloyloxyethyl phosphate
tris-2-acryloyloxyethyl phosphate
tris-2-methacryloyloxyethyl phosphate,
and acid amides, such as
dimethylene-bis-(meth)acrylamide
tetramethylene-bis-(meth)acrylamide
trimethylhexamethylene-bis-(meth)acrylamide
tri(meth)acryloyldiethylenetriamine and similar compounds.

In general, the emphasis among the components to be polymerized is on compounds with one or two olefinic double bonds in the molecule. The additional use of higher unsaturated components is not excluded, but it must be kept in mind that their presence can lead to embrittling of the hardened compositions.

Another essential element of the invention consists in the use of inhibitors or stabilizers against anionic polymerization. It was found that organoboron compounds, particularly boron alkyls, have a polymerization initiating effect, even in the complete absence of traces of oxygen. This polymerization process is, however, much slower than the radical reaction process started by oxygen. Obviously we are dealing in this reaction mechanism with a mild anionic polymerization which can be started by a temperature increase. As it will be described below, the invention deliberately makes use of this double possibility of starting the reaction by organoboron compounds.

For the stability of the reactive adhesive compositions according to the invention, it is thus important to stop or prevent the anionic polymerization effect and the resulting thickening of the reaction mass at the desired time. This is achieved according to the invention by the use of inhibitors or stabilizers against anionic polymerization.

Such inhibitors or stabilizers are particularly the compounds which are also suitable for stabilizing α-cyanacrylic acid esters, for example, acid gaseous substances, such as $SO_2$, $NO_2$, NO, $CO_2$, HCl and HF. Furthermore, in this connection as possible inhibitors or auxiliary inhibitors against premature hardening of the mixtures, are mentioned phosphoric acid, boric acid, boric acid ester, sulfonic acids or sultones, carboxylic acids, such as (meth)acrylic acid, acetic acid, trichloroacetic acid and trifluoroacetic acid, carboxylic acid anhydrides or carboxylic acid esters with alcohols having a free hydroxyl, such as hydroxyethyl methacrylate, phosphorus pentoxide.

In many cases it may be advisable to use as inhibitors against anionic polymerization, those components which are reactive in a radical polymerization and are thus incorporated in the hardening reaction mass. Suitable here are particularly free carboxylic acids with olefinic double bonds, especially lower alkenoic acids, such as acrylic acid and/or methacrylic acid. Their addition in single-component reaction adhesives according to the invention is, therefore, of multiple significance. As known, free carboxyl groups present in the adhesive mass improves its adhesive strength and at the same time the free acids stabilize the reactive single-component mixtures against an undesired anionic polymerization.

Substances acting in the mixture as complexing or sequestering agents, like amines and esters, such as pyridine, propylamine, butylamine, allylamine, diisopropylamine, N,N-dimethyl toluidine, methyl benzoate or ethyl benzoate or anisic acid methyl esters or ethyl esters can also have a favorable effect on the stability.

In general, it must be made sure that premature radical polymerization is also prevented. Here, hydrides, like sodium borohydride, lithium aluminum hydride and calcium hydride are suggested. Furthermore,
cumene
hydroquinone
2,6-di-tert.-butyl-p-cresol
2,6-di-tert.-butyl-4-methoxyphenol bis-(2-hydroxy-3-tert.butyl-5-methyl-phenyl)-
methane
bis-(3,5-di-tert.-butyl-4-hydroxyphenyl)-methane
galvinoxyl
bis-(2-hydroxy-3-tert.-butyl-5-methyl-phenyl)-sulfide
bis-(3-tert.-butyl-4-hydroxy-5-methylphenyl)-sulfide,
or also diphenylamine
N,N'-di-phenyl-p-phenylenediamine
phenothiazine, 2-phenyl-benzimidazole
aniline
dinitrobenzene
2-nitro-60-naphthol
tetraphenylethylene, and
triphenylmethane can be used.

Strong antioxidants are particularly effective in preventing a radical polymerization. Examples are galvinoxyl, copper-II dibutyldithiocarbamate, phenothiazine, and zinc diethyldithiocarbamate. In another preferred embodiment of the invention, however, this final stabilization against radical polymerization is effected by a practically quantitative elimination of unavoidably introduced oxygen traces by means of boron hydride compounds, particularly by the addition of organo-borohydrides, like dialkyl boron monohydrides. The boron hydride bond destroys the oxygen traces practically completely, due to their great reducing capacity. The selection of the amount of organo-borohydride compounds to be added is not critical. It can be effected in excess. The excess amount of organo-borohydride reacts with the olefin components of the reaction mixture to form a boron alkyl compound, which in turn takes over the function of the starter.

The unpolymerized compositions according to the invention should as a rule have a fluid or spreadable consistency to facilitate their application. Particularly suitable is a viscosity range of about 200 to 100,000 mPas, values in the range of about 1,000 to 20,000 mPas being of particular importance. Suitable adhesives have viscosities in the range of several thousand mPas. The fluid or spreadable consistency is as a rule based on the nature of the polymerizable monomer components. Frequently these are liquids which flow easily at room temperature and which must be thickened to obtain an adhesive consistency. This thickening is obtained by using preferably homogeneously miscible polymeric components, such as polymers of (meth)-acrylic acid derivatives, corresponding copolymers, polyvinyl acetate, chlorosulfonated polypropylene, polychloroprene, polyurethanes, etc.

It is difficult, however, to liberate separately produced polymers from residual oxygen traces in such a way that they do not start undesired secondary reactions in the substance mixture. It was, therefore, found particularly advantageous to produce this thickening polymeric portion in situ by partial polymerization of the selected monomers or monomeric mixture. To this end, the relatively slowly acting anionic polymerization started by organoboron compounds, particularly boron alkyls, can be employed. Here the selected monomer mixture is thus prepolymerized by boron alkyls under complete exclusion of oxygen, at first without any addition of inhibitors, until the desired viscosity for bonding purposes has been obtained. Subsequently, the inhibitor against anionic polymerization is added, so that the further thickening of the reaction mixture is prevented. Such mixtures are stable over long periods of time, with positive exclusion of oxygen or air, but they still can react at any time when they come in contact with air. In a similar manner it is also possible to thermally prepolymerize the highly purified monomer mixture which contains neither initiators nor inhibitors and then to add the initiators and inhibitors.

In many cases it is advisable to add additional auxiliary substances, like fillers, such as quartz meal, etc. Finally it may be advisable to color the mixture with suitable dyes or pigments. It is important that all additives are actually free of oxygen or at least as far as possible free of oxygen.

Since total exclusion of oxygen or air cannot as a rule be achieved in practice, the absence of which is a prerequisite for the stability of the single component mixtures, a final stabilization against radical polymerization is provided. As mentioned above, highly effective antioxidants can be used for this purpose, but care must be taken here that these stabilizing components are not present in considerable excess, otherwise the application of the unpolymerized compositions or their desired aerobic hardening could be impaired. The above-mentioned preferred method of the final stabilization according to the invention is the addition of borohydride compounds, which reduce at first the unavoidably introduced oxygen traces, and thus deactivate them, while the excess borohydride compounds form additional starter compounds. In carrying out this embodiment of the production method according to the invention, it may be advisable to add a substantial portion of the boron-containing starter compounds, for example, a quarter to two-thirds of this component, to the reaction mixture in the last stage of the final stabilization against radical polymerization.

Particularly interesting results are obtained with the new reaction adhesives according to the invention in the field of medical applications, particularly in bonding bones, as well as in the field of dentistry. Despite the difficulties of completely drying and/or cleaning the elements to be bonded with each other on the surfaces to be covered with the adhesive, bonds of surprisingly good strength can be obtained.

The new adhesives are characterized in that they have a high hardening rate at room temperature and also form bonds in a short time on a number of different surfaces. It is to be stressed that a rapid and firm adhesion can also be achieved on surfaces which are not completely dry. The adhesives can thus be used as so-called structural adhesives for bonding metals, wood, glass, ceramic materials and plastics. Compared to other reactive liquid adhesives, like the cyanacrylates, the systems according to the invention have the advantage that they are practically completely independent of the selection of the monomer or monomer mixture. They offer thus a wide range in the use of monomer mixtures. Good cohesion and good adhesion on different surfaces are ensured. Hardening takes place on practically all surfaces, regardless of the metal, by atmospheric oxygen which is available everywhere in practically constant concentration.

For the production of the single-component reactive unpolymerized mixtures, the required amount of the dried monomer or monomeric mixture is preferably degassed in a high vacuum apparatus, distilled if necessary, and subsequently recondensed into a storage vessel, if desired. The mixtures can also be pretreated for further cleaning with hydrogenating substances, such as $NaBH_4$, $LiAlH_4$, $CaH_2$ or with an organoboron hydride compound, as it was described above for the final step to eliminate oxygen traces. At least a part of the boron-containing starter or the borohydride compound which reacts with the monomer mixture is introduced into the oxygen-free monomer mixture. If necessary, the viscosity of the mixture is raised into the desired range by controlled anionic polymerization under the influence of the organoboron compounds. Finally, the inhibitors against ionic polymerization are added, and this stage is thus stopped. If desired, additional additives, like fillers, pigments and the like are added to the mixture. Finally the stabilization against radical polymerization is effected by eliminating the oxygen traces by the addition of borohydride compounds and/or by the addition of antioxidants.

For the production of reaction adhesives according to the invention, the following reactants or potential reactants can be added, for example to the oxygen-free monomer mixture under pure nitrogen:

| Percent by Weight | |
|---|---|
| 0.01% to 15% | of boron compound |
| 0.01% to 10%, particularly 0.01% to 5%, | of inhibitors against ionic polymerization |
| 0 to 40% | of a polymer |
| 0.01% to 3% | of a radical inhibitor. |

The reactive unpolymerized mixtures must be stored under exclusion of atmospheric oxygen. The atmospheric oxygen acting on applied portions of the reaction mass starts the polymerization and leads to hardening.

The following examples are intended to illustrate the invention and are not to be construed as limiting the invention thereto.

EXAMPLE I

Under exclusion of oxygen, 12.2 gm of 9-borabicyclo[3,3,1]-nonane (hereinafter "9-BBN") were dissolved in 100 ml of anhydrous, degassed tetrahydrofuran. Under exclusion of oxygen, 8.6 gm of degassed methyl methacrylate were added dropwise to the solution. The tetrahydrofuran was removed under vacuum after the completion of the exothermic reaction.

Four grams of polymethyl methacrylate, which had been polymerized by radical-initiation with azoisobutyronitrile, under exclusion of oxygen, were dissolved in 4.5 gm of oxygen-free methyl methacrylate and 0.5 gm of oxygen-free methyacrylic acid in a glovebox. Twenty mg of $NaBH_4$, 0.35 gm of oxygen-free dimethyltoluidine, and 0.5 gm of the reaction product of 9-BBN with methyl methacrylate were added to the mixture. The container was sealed and stored under nitrogen.

After ten hours to exposure to the air, the resulting mixture was used to bond beechwood pieces according to DIN 68602, which pieces were torn apart after 24 hours. The average tensile and shear strength was 8.3 $N/mm^2$. Furthermore, sandblasted and degreased sheet iron pieces were bonded according to DIN 53281/53282 and torn apart after 24 hours. The average tensile and shear strength was 14.3 $N/mm^2$.

EXAMPLES 2 TO 7

The adhesive mixtures below were prepared using procedures analogous to that of Example 1. The boron-containing initiators, the adjuvants, including thickeners, and the methyl methacrylate monomer components were as follows.

TABLE I

| Example | Initiator | Adjuvants | Methyl Methacrylate |
|---|---|---|---|
| 2 | 0.3 gm 9-BBN | 20 mg $NaBH_4$ 0.35 mg methyl benzoate | 10 ml |
| 3 | 0.3 gm 9-BBN | 20 mg $NaBH_4$ 0.4 gm methyl anisate | 10 ml |
| 4 | 0.3 gm 9-BBN | 20 mg $NaBH_4$ 0.35 gm dimethyltoluidine | 10 ml |
| 5 | 0.3 gm 9-BBN | 20 mg hydroquinone 0.4 gm ethyl anisate | 7 gm |
| 6 | 0.3 gm 9-BBN | 20 mg hydroquinone 0.35 gm dimethyltoluidine | 7 gm |
| 7 | 0.3 gm tri-n-butylboroxine | 20 mg hydroquinone | 7 gm |

The adhesive mixture of Examples 2 to 7 were tested according to DIN 68602 and 53281/53282, described above. Bonding was measured at the time, in hours, after preparation of the respective adhesive mixtures, and the sheet iron and beechwood test pieces, respectively, were torn apart after 24 hours. The results were as follows.

TABLE II

| Example | Bonding (Hours) | Tensile and Shear Strength | |
|---|---|---|---|
| | | Iron | Beechwood |
| 2 | 200 | 23.7 | 6.0 |
| 3 | 200 | 30.2 | 8.4 |
| 4 | 150 | 26.0 | — |
| 5 | 150 | 15.7 | — |
| 6 | 150 | 18.6 | — |
| 7 | 75 | 11.0 | — |

EXAMPLE 8

(a) Three hundred millileters of methyl methacrylate were dried with sodium sulfate, degassed at $10^{-3}$ torr in high-vacuum equipment, and condensed with 2.2 gm of 9-BBN. After one hour, the product was again degassed and condensed again with 9 gm of 9-BBN. This solution was stored for 24 hours, until the viscosity rose to the point that was well suited for the bonding of metals.

(b) Under complete exclusion of oxygen, 1.0 gm of absolutely oxygen-free methacrylic acid was added to 25 ml of the solution from Step (a), followed by the addition of 0.75 gm of 9-BBN. This mixture was stored for 30 days, and the viscosity did not change during this storage period. Sheet iron and aluminum, respectively, were bonded according to DIN 68602 with this mixture, and after 12 hours, tensile and shear strenghts of 26 and 18 $N/mm^2$, respectively, were obtained.

EXAMPLE 9

Under absolute exclusion of oxygen, 0.25 gm of pyridine, 2.2 gm of methacrylic acid, and 0.75 gm of 9-BBN were added to 25 ml of stock solution from Example 8(a). After 30 days of storage, the following tensile and shear strengths were obtained with this adhesive according to DIN 68602:

Iron: 20 $N/mm^2$

Aluminum: 8 $N/mm^2$

The test pieces were torn apart twelve hours after bonding.

EXAMPLE 10

Under absolute exclusion of oxygen, 0.24 gm of pyridine and 0.75 gm of 9-BBN were added to 25 ml of the stock solution from Example 8(a). After storage of the adhesive for 30 days, the following tensile and shear strengths were obtained according to DIN 68602:
Iron: 15 N/mm$^2$
Aluminum: 9 N/mm$^2$
The test pieces were torn apart twelve hours after bonding.

EXAMPLE 11

Under absolute exclusion of oxygen, 100 mg of galvinoxyl were added to 25 ml of the stock solution from Example 8(a). After storage of the adhesive for 30 days, the following tensile and shear strengths were obtained according to DIN 68602:
Iron: 19 N/mm$^2$
Aluminum: 15 N/mm$^2$
The test pieces were torn apart twelve hours after bonding.

EXAMPLE 12

One hundred seventy milliliters of methyl methacrylate were dried with sodium sulfate, degassed at $10^{-3}$ torr in high-vacuum equipment, and condensed with 2.2 gm of 9-BBN. Under absolute exclusion of oxygen, 15 gm of oxygen-free, condensable hydroxyethyl methacrylate were added to this solution. This mixture was allowed to stand for 72 hours, until a higher viscosity was reached, which viscosity was well suited for the bonding of metals.

Under absolute exclusion of oxygen, 0.48 gm of pyridine and 0.75 gm of 9-BBN were added to 25 ml of this solution prepared in a glovebox. The resulting mixture was allowed to stand for 30 days, and the viscosity did not change during this storage period. Sheet iron and aluminum, respectively, were bonded according to DIN 68602, and the following strengths were obtained:
Iron: 28 N/mm$^2$
Aluminum: 19 N/mm$^2$
The test pieces were torn apart twelve hours after bonding.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A stable, fluid or spreadable, aerobically-hardening adhesive, storable without hardening under exclusion of oxygen, containing polymerizable olefinically-unsaturated compounds and an amount sufficient to initiate polymerization of an organoboron compound initiator, in the form of an aerobically-hardening single component mixture, consisting essentially of:
   (a) at least one organoboron compound capable of initiating the polymerization of ethylenically-unsaturated compounds in the presence of oxygen, in an amount sufficient to initiate the polymerization,
   (b) at least one polymerizable compound containing at least one ethylenic double bond with a molecular weight of between 63 and 10,000,
   (c) at least one compound capable of inhibiting and/or stabilizing anionic polymerization, in an amount sufficient to inhibit and/or stabilize anionic polymerization,
   (d) at least one compound capable of inhibiting and/or stabilizing radical polymerization, in an amount sufficient to inhibit and/or stabilize radical polymerization, and
   (e) optionally, other conventional auxiliary substances for aerobically hardening adhesives.

2. The aerobically-hardening adhesive of claim 1 wherein said organoboron compound capable of initiating the polymerization is a member selected from the group consisting of boron alkyls, boron hydrocarbon aryls, boroxines, and reaction products of dihydroxy hydrocarbon aromatic compounds with boron hydride.

3. The aerobically-hardening adhesive of claim 1 or 2 which hardens in the presence of air during application.

4. The aerobically-hardening adhesive of claim 1 or 2 wherein said at least one polymerizable compound has a molecular weight of between 72 and about 4,000 and is a member selected from the group consisting of methacrylic acid compounds and acrylic acid compounds.

5. The aerobically-hardening adhesive of claim 4 wherein said organoboran compound is a boron alkyl compound.

6. The aerobically-hardening adhesive of claim 4 wherein said methacrylic acid compounds and acrylic acid compounds are selected from the group consisting of esters of acrylic acid with monohydric or polyhydric alcohols, acrylamide, substituted acrylamides, esters of methacrylic acid with monohydric or polyhydric alcohols, methacrylamide and substituted methacrylamides.

7. The aerobically-hardening adhesive of claim 6 having a content of from 0.01% to 10% by weight of the polymerizable component (b) of acrylic acid or methacrylic acid.

8. The aerobically-hardening adhesive of claim 7 wherein the amount of said acrylic acid or methacrylic acid is from 0.01% to 5% by weight of the polymerizable component (b).

9. The aerobically-hardening adhesive of claim 1 wherein (e) includes thickeners, auxiliary monomers, dyes and pigments.

10. The aerobically-hardening adhesive of claim 9 wherein said thickeners are polymers homogeneously miscible with said polymerizable compound component (b).

11. The aerobically-hardening adhesive of claim 10 wherein said polymers are polymers of a polymerizable compound having a molecular weight of between 72 and about 4,000 and being a member selected from the group consisting of methacrylic acid compounds and acrylic acid compounds.

12. The aerobically-hardening adhesive of claim 11 wherein said thickener is a polymer of said methacrylic acid compounds and acrylic acid compounds prepared in situ under the initiation of said organoboron compounds of component (a).

13. The aerobically hardening adhesive of claim 1 or 2 wherein said at least one organoboron compound of component (a) is present in an amount of up to about 15% by weight, based on the total amount of the polymerizable component (b).

14. The aerobically-hardening adhesive of claim 13 wherein said component (a) is present in an amount of from 0.1% to 10% by weight, based on the total amount of the polymerizable component (b).

15. The aerobically-hardening adhesive of claim 1 or 2 having a viscosity of from about 200 to 100,000 mPas.

16. The aerobically-hardening adhesive of claim 15 having a viscosity of from about 1,000 to 20,000 mPas.

17. The method for the production of the aerobically-hardening adhesive of claim 1 or 2 comprising the steps of adding said organoboron compounds of component (a) to a liquid, at least one polymerizable compound of component (b), which contains no substantial portion of free acid groups, under the exclusion of oxygen, raising the viscosity of the mixture into the desired range by aging, subsequently adding inhibitors against anionic polymerization, stabilizing the mixture against radical polymerization, and recovering said aerobically-hardening adhesive.

18. The method of claim 17 wherein said stabilizing of the mixture against radical polymerization is effected by the addition of boron hydride or organoboron hydride compounds.

19. The method of claim 18 wherein said boron hydride or organoboron hydride compounds are added in excess over the amount necessary to reduce any traces of oxygen present.

20. The method of claim 17 wherein said inhibitors against anionic polymerization are acids.

21. The method of claim 20 wherein said acids are copolymerizable olefinically-unsaturated carboxylic acids.

22. The aerobically-hardening adhesive of claim 2 wherein said organoboron compound is 9-borabicyclo-(3,3,1)-nonane.

23. The aerobically-hardening adhesive of claim 12 wherein said organoboron compound is 9-borabicyclo-(3,3,1)-nonane.

* * * * *